United States Patent [19]

Thurkauf et al.

[11] Patent Number: 5,646,279

[45] Date of Patent: Jul. 8, 1997

[54] SUBSTITUTED 4-PIPERAZINYLMETHYL 2-PHENYLIMIDAZOLES; DOPAMINE RECEPTOR SUBTYPE SPECIFIC LIGANDS

[75] Inventors: Andrew Thurkauf, Danbury; Alan Hutchison, Madison, both of Conn.

[73] Assignee: Neurogen Corporation, Branford, Conn.

[21] Appl. No.: 457,036

[22] Filed: Jun. 1, 1995

Related U.S. Application Data

[63] Continuation of Ser. No. 344,552, Nov. 23, 1994, abandoned, which is a continuation-in-part of Ser. No. 313,435, Sep. 27, 1994, which is a continuation-in-part of Ser. No. 81,317, Nov. 8, 1993, Pat. No. 5,428,164, which is a continuation-in-part of Ser. No. 635,256, Dec. 28, 1990, Pat. No. 5,159,083.

[51] Int. Cl.$^6$ ............... C07D 403/04; C07D 403/06; C07D 233/64; A61K 31/415

[52] U.S. Cl. ............... 544/295; 544/360; 544/364; 544/370

[58] Field of Search ............... 548/343.1, 348.5; 546/210; 544/370, 295, 360, 364

[56] References Cited

U.S. PATENT DOCUMENTS

| | | | |
|---|---|---|---|
| 3,304,306 | 2/1967 | Werner et al. | 546/210 |
| 3,491,018 | 1/1970 | Archer | 544/370 |
| 4,080,503 | 3/1978 | Kummer et al. | 548/316 |
| 4,404,382 | 9/1983 | Gall | 544/370 |
| 4,665,023 | 5/1987 | Deneke et al. | 435/28 |
| 5,043,447 | 8/1991 | Pascal et al. | 544/370 |
| 5,159,083 | 10/1992 | Thurkauf et al. | 548/335.5 |
| 5,292,669 | 3/1994 | Guder et al. | 435/18 |
| 5,296,609 | 3/1994 | McCort et al. | 548/325.1 |
| 5,312,927 | 5/1994 | Takada et al. | 548/325.1 |
| 5,378,847 | 1/1995 | McCort et al. | 544/370 |
| 5,380,865 | 1/1995 | Cramp et al. | 548/329.5 |
| 5,428,164 | 6/1995 | Thurkauf et al. | 544/295 |

FOREIGN PATENT DOCUMENTS

| | | | |
|---|---|---|---|
| 0353606 | 2/1990 | European Pat. Off. | 548/343.5 |
| 0379992 | 8/1990 | European Pat. Off. | 546/210 |
| 93-012093 | 6/1993 | WIPO | 544/370 |

*Primary Examiner*—Floyd D. Higel
*Attorney, Agent, or Firm*—McDonnell Boehnen Hulbert & Berghoff

[57] ABSTRACT

Disclosed are compounds and the pharmaceutically acceptable salts thereof useful in the diagnosis and treatment of affective disorders such as schizophrenia and depression as well as certain movement disorders such as Parkinsonism and useful in treating the extrapyramidal side effects associated with the use of conventional neuroleptic agents, which compounds have the formula:

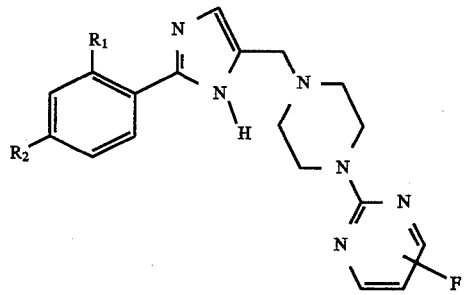

where $R_1$ and $R_2$ are independently represent hydrogen or inorganic groups.

3 Claims, 2 Drawing Sheets

Compound 1

Compound 8

Compound 16

Compound 19

Compound 21

Compound 24

Compound 26

Compound 23

Compound 25

Compound 71

Compound 28

Compound 70

SUBSTITUTED 4-PIPERAZINYLMETHYL 2-PHENYLIMIDAZOLES; DOPAMINE RECEPTOR SUBTYPE SPECIFIC LIGANDS

This is a continuation application of U.S. Ser. No. 08/344,552, filed Nov. 23, 1994 now abandoned, which is a continuation-in-part of U.S. patent application Ser. No. 08/313,435, filed Sep. 27, 1994, which is a continuation-in-part of U.S. patent application Ser. No. 08/081,317, filed Nov. 8, 1993, now U.S. Pat. No. 5,428,164 which is a continuation-in-part of U.S. patent application Ser. No. 07/635,256, filed Dec. 28, 1990 (now U.S. Pat. No. 5,159,083).

BACKGROUND OF THE INVENTION

1. Field of the Invention

This invention relates to certain aminomethyl phenylimidazole derivatives which selectively bind to brain dopamine receptor subtypes. This invention also relates to pharmaceutical compositions comprising such compounds. It further relates to the use of such compounds in treating affective disorders such as schizophrenia and depression as well as certain movement disorders such as Parkinsonism. Furthermore compounds of this invention may be useful in treating the extrapyramidyl side effects associated with the use of conventional neuroleptic agents. The interaction of aminomethyl phenylimidazole derivatives of the invention with dopamine receptor subtypes is described. This interaction results in the pharmacological activities of these compounds.

2. Description of the Related Art

Schizophrenia or psychosis is a term used to describe a group of illnesses of unknown origin which affect approximately 2.5 million people in the United States. These disorders of the brain are characterised by a variety of symptoms which are classified as positive symptoms (disordered thought, hallucinations and delusions) and negative symptoms (social withdrawal and unresponsiveness). These disorders have an age of onset in adolescence or early adulthood and persist for many years. The disorders tend to become more severe during the patient's lifetime and can result in prolonged institutionalization. In the U.S. today, approximately 40% of all hospitalized psychiatric patents suffer from schizophrenia.

During the 1950's physicians demonstrated that they could successfully treat psychotic patients with medications called neuroleptics; this classification of antipsychotic medication was based largely on the activating (neuroleptic) properties of the nervous system by these drugs. Subsequently, neuroleptic agents were shown to increase the concentrations of dopamine metabolites in the brain suggesting altered neuronal firing of the dopamine system. Additional evidence indicated that dopamine could increase the activity of adenylate cyclase in the corpus striatum, an effect reversed by neuroleptic agents. Thus, cumulative evidence from these and later experiments strongly suggested that the neurotransmitter dopamine was involved in schizophrenia.

One of the major actions of antipsychotic medication is the blockade of dopamine receptors in brain. Several dopamine systems appear to exist in the brain and at least five classes of dopamine receptors appear to mediate the actions of this transmitter. These dopamine receptors differ in their pharmacological specificity and were originally classified upon these differences in the pharmacology of different chemical series. Butyrophenones, containing many potent antipsychotic drugs were quite weak at the dopamine receptor that activated adenylate cyclase (now known as a D1 dopamine receptor). In contrast they labelled other dopamine receptors (called D2 receptors) in the subnanomolar range and a third type D3 in the nanomolar range. Two additional receptor subtypes have also been identified. D5 which is somewhat similar to D1 receptor type and D4 which is closely related to D3 and D2 receptor types. Phenothiazines possess nanomolar affinity for all three types of dopamine receptors. Other drugs have been developed with great specificity for the D1 subtype receptor, and for the D2 subtype receptor.

Recently, a new group of drugs (such as sulpiride and clozapine) have been developed with a lesser incidence of extrapyramidal side effects than classical neuroleptics. In addition, there is some indication that they may be more beneficial in treating negative symptoms in some patients. Since all D2 blockers do not possess a similar profile, hypotheses underlying the differences have been investigated. The major differences have been in the anticholinergic actions of the neuroleptics as well as the possibility that the dopamine receptors may differ in motor areas from those in the limbic areas thought to mediate the antipsychotic responses. The existence of the D3, D4 and D5 and other as yet undiscovered dopamine receptors may contribute to this profile. Some of the atypical compounds possess similar activity at both D2 D3 and D4 receptors. The examples of this patent fall into this general class of molecules.

Using molecular biological techniques it has been possible to clone cDNAs coding for each of the pharmacologically defined receptors. There are at least two forms of D1 which have been identified as D1 and D5, and two forms of D2, identified now as D2 and D4 dopamine receptors. In addition, there is at least one form of D3 dopamine receptor. Examples from the aminomethyl phenylimidazole series of this patent possess differential affinities for each receptor subtype.

Schizophrenia is characterized by a variety of cognitive dysfunctions; schizophrenic patients perform less well than other groups on most cognitive or attentional tasks. The positive and negative symptom dimensions of schizophrenia are also associated with distinct cognitive deficits. In general, positive symptoms (disordered thought processes, hallucinations and decisions) are related to auditory processing imairments including deficits in verbal memory and language comprehenion. Negative symptoms (social withdrawal and unresponsiveness) are related more to visual/motor dysfunctions including poorer performance on visual memory, motor speed and dexterity tasks.

These disorders have an age of onset in adolescence or early adulthood and persist for many years. The interaction of frontal and septo-hippocampal brain systems, and failures of information processing and self monitoring have been theorized as the basis of positive symptoms. Negative symptoms are thought to arise from abnormalities in the interactions of frontal and striatal systems. Since cognitive disturbances are present in most of the patients diagnosed as having schizophrenia, it has been theorized that to understand the pathogenesis and etiology of schizophrenia, one must understand the basic dysfunction of the cognitive disorder.

The cognitive disturbances found in schizophrenia include, but are not limited to, various verbal and visual deficits. There are various neurocognitive tasks for both animals and humans that have been developed to assess memory deficits, as well as memory enhancements, of various treatments. Many of the neurocognitive behavioral tasks are modulated or mediated by eural activity within the hippocampal brain system noted above.

Drug substances that interact with the hippocampus are capable of modulating memory in animals. Certain memory paradigms employed in animals have construct and predictive validity for memory assessment in humans. In animals (rodents), paradigms such as the Step-Down Passive Avoidance Task assay or the Spatial Water Maze Task assay reliably detect deficits produced by certain drugs in humans. For example, commonly prescribed benzodiazepine anxiolytics and sedative hypnotics are known to produce memory impairment in humans, including varying degrees of anterograde amnesia (depending on the exact drug). In the step-down passive avoidance paradigm, these very same drugs disrupt the memory of animals given the compounds during the information acquisition or processing period. Likewise, benzodiazepines disrupt information processing and memories in the spatial water maze task in rodents. Thus, these animal models can be used to predict the memory impairing effects of certain compounds in humans. Conversely, these same animal models can predict the memory improving or enhancing effects of compounds in humans. Although fewer in number, drugs that improve memory in humans (e.g., Nootroprice, Beta carbolines) produce memory enhancing effects in rats in these models. Therefore, the spatial water maze and step-down passive avoidance paradigms in rodents are useful in predicting memory impairing and memory enhancing effects of test compounds in humans.

SUMMARY OF THE INVENTION

This invention provides novel compounds of Formula I which interact with dopamine receptor subtypes.

The invention provides pharmaceutical compositions comprising compounds of Formula I. The invention also provides compounds useful in treating affective disorders such as schizophrenia and depression as well as certain movement disorders such as Parkinsonism. Furthermore compounds of this invention may be useful in treating the extrapyramidyl side effects associated with the use of conventional neuroleptic agents. Accordingly, a broad embodiment of the invention is directed to a compound of Formula I:

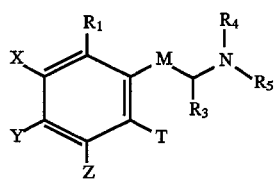

where $R_1$ and T are
the same or different and represent hydrogen, halogen, hydroxy, straight or branched chain lower alkyl having 1–6 carbon atoms, or straight or branched chain lower alkoxy having 1–6 carbon atoms:

M is

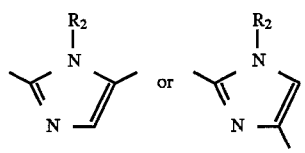

and $R_2$ is
hydrogen or, straight or branched chain lower alkyl having 1–6 carbon atoms, or $R_1$ and $R_2$ together may represent —$(CH_2)_{n1}$— where $n_1$ is 1, 2, or 3;

X and Z are
the same or different and represent hydrogen, halogen, hydroxy, straight or branched chain lower alkyl having 1–6 carbon atoms, straight or branched chain lower alkoxy having 1–6 carbon atoms or $SO_2R_6$ where $R_6$ is straight or branched chain lower alkyl having 1–6 carbon atoms;

Y is
hydrogen, amino, halogen, or straight or branched chain lower alkyl having 1–6 carbon atoms;

$R_3$ is
hydrogen or, straight or branched chain lower alkyl having 1–6 carbon atoms, or $R_3$ and $R_4$ together may represent —$(CH_2)_{n2}$— where $n_2$ is 3 or 4;

$R_4$ and $R_5$ are
the same or different and represent hydrogen, straight or branched chain lower alkyl having 1–6 carbon atoms, aryl straight or branched chain lower alkyl having 1–6 carbon atoms or $R_2$ and $R_5$ together may represent —$(CH_2)_{n3}$— where $n_3$ is 2 or 3; or $NR_4R_5$ together represent
2-(1,2,3,4-tetrahydroisoquinolinyl), either unsubstituted or mono or disubstituted with halogen, hydroxy, straight or branched chain lower alkyl having 1–6 carbon atoms, or straight or branched chain lower alkoxy having 1–6 carbon atoms; or $NR_4R_5$ represents

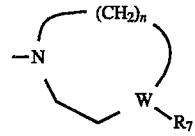

where

W is
N or CH;

$R_7$ is
hydrogen, phenyl, arylalkyl, pyridyl or pyrimidinyl, unsubstituted or mono or disubstituted with halogen, hydroxy, straight or branched chain lower alkyl having 1–6 carbon atoms, or straight or branched chain lower alkoxy having 1–6 carbon atoms; or W-$R_7$ is
oxygen or sulfur; and n is
1, 2, or 3.

These compounds are highly selective partial agonists or antagonists at brain dopamine receptor subtypes or prodrugs thereof and are useful in the diagnosis and treatment of affective disorders such as schizophrenia and depression as well as certain movement disorders such as Parkinsonism. Furthermore compounds of this invention may be useful in treating the extrapyramidyl side effects associated with the use of conventional neurolepticagents.

The compounds of the invention, such as, for example, 2-Phenyl-4(5)-[(4-(2-pyrimidinyl)piperazin-1-yl)-methyl]-imidazole dihydrochloride (compound 23), 2-Phenyl-4(5)-[(4-(2-pyridl)piperazin-1-yl)-methyl]-imidazole dihydrochloride (Compound 24), and 2-Phenyl-4(5)-[(4-phenyl-piperazin-1-yl)-methyl]-imidazole dihydrochloride (Compound 45), are antagonists binding to dopamine D4 receptors in both the rat and human hippocampus.

As noted above, the hippocampus is associated with both schizophrenia, and general memory processes in humans. In rodents, compound 23 produces memory enhancing effects in both the step-down passive avoidance assay as well as in the spatial water maze assay. Without being bound by a particular theory, it is believed that the $D_4$ receptors located in the hippocampus mediate the memory enhancing effects of the compounds of the invention. Therefore, since (1) compound 23 is active in animal models that are predictive of cognition enhancement, and specifically enhancement of memory and learning, and (2) compound 23 binds to $D_4$ receptors in the hippocampus, the $D_4$ class of dopamine antagonists, including the compounds of the invention, are useful for enhancing memory in humans.

Thus, the invention further provides methods for enhancing cognition, and specifically learning and memory, in mammals. These methods comprise administering to a mammal such as a human a compound of the invention, such as, for example, a compound of formula V, VI, VII, or XII, in an amount effective to enhance cognition.

DETAILED DESCRIPTION OF THE INVENTION

Figure 1A:
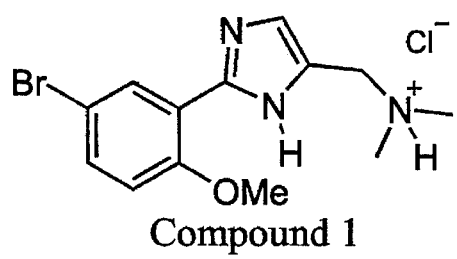
FIGS. 1A–1L show representative aminomethyl phenylimidazoles of the present invention.
Figure 1B:
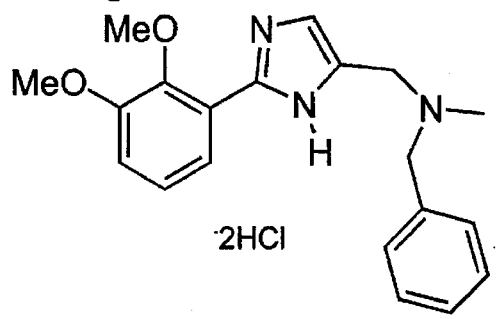
Figure 1C:
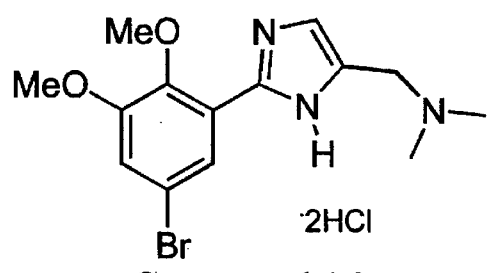
Figure 1D:
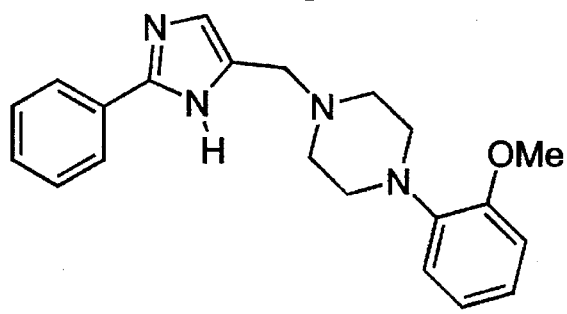
Figure 1E:
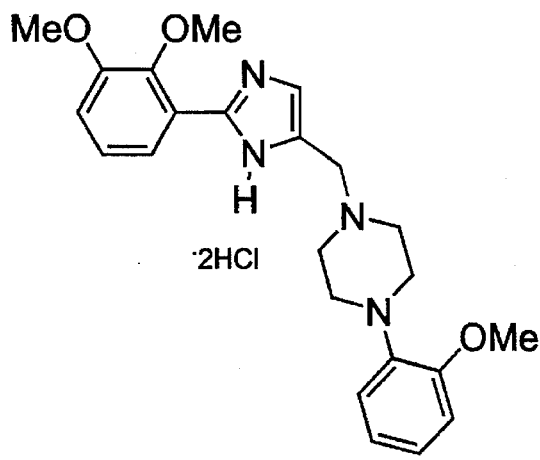
Figure 1F:
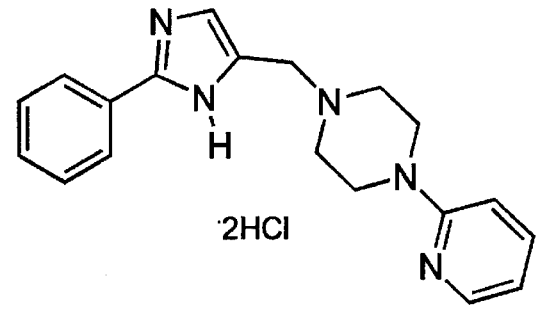
Figure 1G:
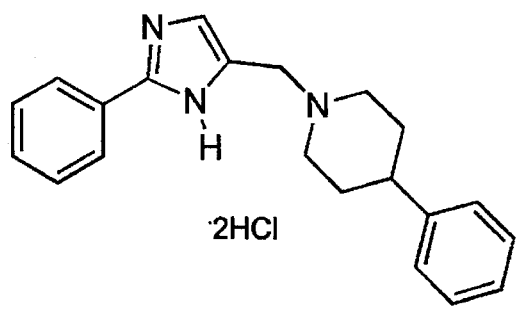
Figure 1H:
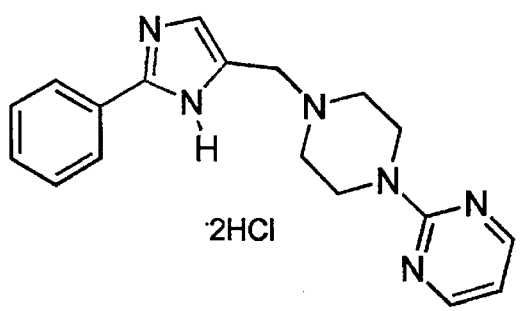
Figure 1I:
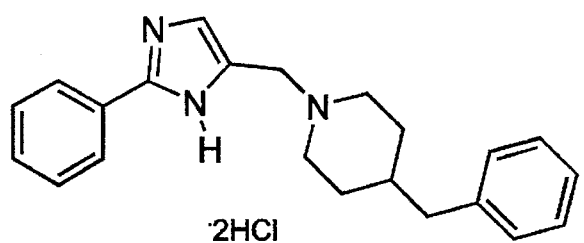
Figure 1J:
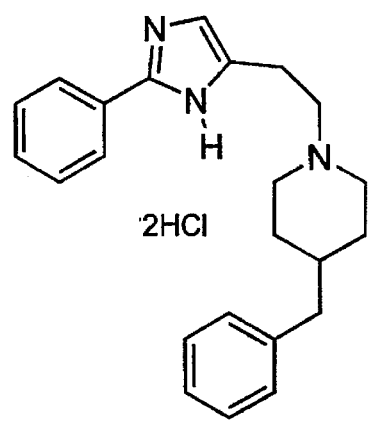
Figure 1K:
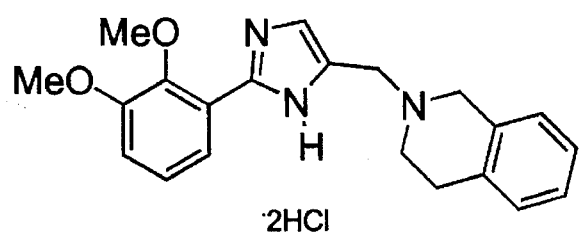
Figure 1L:
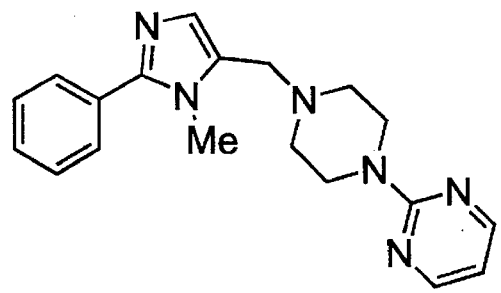

The novel compounds encompassed by the instant invention can be described by general formula I:

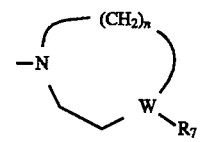

where $R_1$ and T are
the same or different and represent hydrogen, halogen, hydroxy, straight or branched chain lower alkyl having 1–6 carbon atoms, or straight or branched chain lower alkoxy having 1–6 carbon atoms;

M is

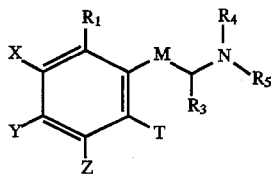

and $R_2$ is hydrogen or, straight or branched chain lower alkyl having 1–6 carbon atoms, or $R_1$ and $R_2$ together may represent —$(CH_2)_{n1}$— where $n_1$ is 1, 2, or 3;

X and Z are
the same or different and represent hydrogen, halogen, hydroxy, straight or branched chain lower alkyl having 1–6 carbon atoms, straight or branched chain lower alkoxy having 1–6 carbon atoms or $SO_2R_6$ where $R_6$ is straight or branched chain lower alkyl having 1–6 carbon atoms;

Y is hydrogen, amino, halogen, or straight or branched chain lower alkyl having 1–6 carbon atoms;

$R_3$ is
hydrogen or, straight or branched chain lower alkyl having 1–6 carbon atoms, or $R_3$ and $R_4$ together may represent —$(CH_2)_{n2}$— where $n_2$ is 3 or 4;

$R_4$ and $R_5$ are
the same or different and represent hydrogen, straight or branched chain lower alkyl having 1–6 carbon atoms, aryl straight or branched chain lower alkyl having 1–6 carbon atoms or $R_2$ and $R_5$ together may represent —$(CH_2)_{n3}$— where $n_3$ is 2 or 3; or $NR_4R_5$ represents
2-(1,2,3,4-tetrahydroisoquinolinyl), either unsubstituted or mono or disubstituted with halogen, hydroxy, straight or branched chain lower alkyl having 1–6 carbon atoms, or straight or branched chain lower alkoxy having 1–6 carbon atoms; or $NR_4R_5$ represents

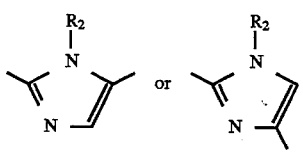

where
W is
N or CH;
$R_7$ is
hydrogen, phenyl, arylalkyl, pyridyl or pyrimidinyl, unsubstitute or mono or disubstituted with halogen, hydroxy, straight or branched chain lower alkyl having 1–6 carbon atoms, or straight or branched chain lower alkoxy having 1–6 carbon atoms; or
W-$R_7$ is
oxygen or sulfur; and
n is
1, 2, or 3.

Preferred compounds of Formula I are those where W is CH and $R_7$ is an arylalkyl, more preferably a benzyl, group.

The present invention further encompasses compounds of Formula II:

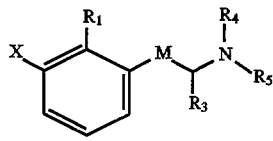

where
$R_1$ is
hydrogen, halogen, hydroxy, straight or branched chain lower alkyl having 1–6 carbon atoms, or straight or branched chain lower alkoxy having 1–6 carbon atoms;

M is

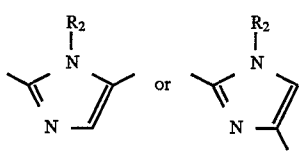

and

R$_2$ is
hydrogen or, straight or branched chain lower alkyl having 1–6 carbon atoms, or R$_1$ and R$_2$ together, may represent —(CH$_2$)$_{n1}$ where n$_1$ is 1, 2, or 3;

X is
hydrogen, halogen, hydroxy, straight or branched chain lower alkyl having 1–6 carbon atoms, straight or branched chain lower alkoxy having 1–6 carbon atoms or SO$_2$R$_6$ where R$_6$ is straight or branched chain lower alkyl having 1–6 carbon atoms;

R$_3$ is
hydrogen or, straight or branched chain lower alkyl having 1–6 carbon atoms, or R$_3$ and R$_4$ together may represent —(CH$_2$)$_{n2}$— where n$_2$ is 3 or 4;

R$_4$ and R5 are
the same or different and represent hydrogen, straight or branched chain lower alkyl having 1–6 carbon atoms, aryl straight or branched chain lower alkyl having 1–6 carbon atoms or R$_2$ and R$_5$ together may represent —(CH$_2$)$_{n3}$— where n3 is 2 or 3; or NR$_4$R$_5$ represents
2-(1,2,3,4-tetrahydroisoquinolinyl), either unsubstituted or mono or disubstituted with halogen, hydroxy, straight or branched chain lower alkyl having 1–6 carbon atoms, or straight or branched chain lower alkoxy having 1–6 carbon atoms; or NR$_4$R$_5$ represents

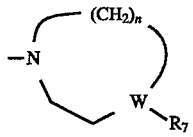

where
W is
N or CH:
R$_7$ is
hydrogen, phenyl, arylalkyl, pyridyl or pyrimidinyl, unsubstitute or mono or disubstituted with halogen, hydroxy, straight or branched chain lower alkyl having 1–6 carbon atoms, or straight or branched chain lower alkoxy having 1–6 carbon atoms; or
W—R$_7$ is
oxygen or sulfur;, and
n is
1, 2, or 3.

Preferred compounds of Formula II are those where W is CH and R$_7$ is an arylalkyl, more preferably a benzyl, group.

The present invention also encompasses compounds of Formula III:

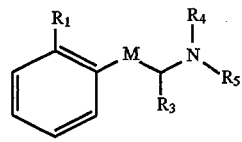

where
R$_1$ is
hydrogen, halogen, hydroxy, straight or branched chain lower alkyl having 1–6 carbon atoms, or straight or branched chain lower alkoxy having 1–6 carbon atoms;

M is

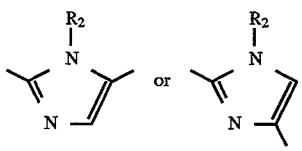

and

R$_2$ is
hydrogen or, straight or branched chain lower alkyl having 1–6 carbon atoms, or R$_1$ and R$_2$ together may represent —(CH$_2$)$_{n1}$ where n$_1$ is 1, 2, or 3;

R$_3$ is
hydrogen or, straight or branched chain lower alkyl having 1–6 carbon atoms, or R$_3$ and R$_4$ together may represent —(CH$_2$)$_{n2}$— where n$_2$ is 3 or 4;

R$_4$ and R$_5$ are
the same or different and represent hydrogen, straight or branched chain lower alkyl having 1–6 carbon atoms, aryl straight or branched chain lower alkyl having 1–6 carbon atoms or R$_2$ and R$_5$ together may represent —(CH$_2$)$_{n3}$— where n$_3$ is 2 or 3; or NR$_4$R$_5$ represents
2-(1,2,3,4-tetrahydroisoquinolinyl), either unsubstituted or mono or disubstituted with halogen, hydroxy, straight or branched chain lower alkyl having 1–6 carbon atoms, or straight or branched chain lower alkoxy having 1–6 carbon atoms; or NR$_4$R$_5$ represents

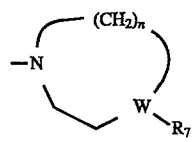

where
W is
N or CH;
R$_7$ is
hydrogen, phenyl, arylalkyl, pyridyl or pyrimidinyl, unsubstitute or mono or disubstituted with halogen, hydroxy, straight or branched chain lower alkyl having 1–6 carbon atoms, or straight or branched chain lower alkoxy having 1–6 carbon atoms; or
W—R$_7$ is
oxygen or sulfur; and
n is
1, 2, or 3.

Preferred compounds of Formula III are those where W is CH and R$_7$ is an arylalkyl, more preferably a benzyl, group.

In addition, the present invention encompasses compounds of Formula IV:

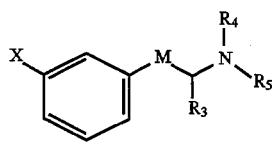

where
M is

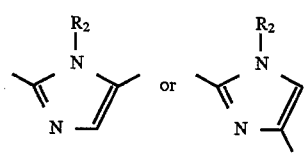

and $R_2$ is hydrogen or, straight or branched chain lower alkyl having 1–6 carbon atoms, or $R_1$ and $R_2$ together may represent —$(CH_2)_{n1}$— where $n_1$ is 1, 2, or 3;

X is
hydrogen, halogen, hydroxy, straight or branched chain lower alkyl having 1–6 carbon atoms, straight or branched chain lower alkoxy having 1–6 carbon atoms or $SO_2R_6$ where $R_6$ is straight or branched chain lower alkyl having 1–6 carbon atoms;

$R_3$ is hydrogen or, straight or branched chain lower alkyl having 1–6 carbon atoms, or $R_3$ and $R_4$ together may represent —$(CH_2)_{n2}$— where $n_2$ is 3 or 4;

$R_4$ and $R_5$ are
the same or different and represent hydrogen, straight or branched chain lower alkyl having 1–6 carbon atoms, aryl straight or branched chain lower alkyl having 1–6 carbon atoms or $R_2$ and $R_5$ together may represent —$(CH_2)_{n3}$— where n3 is 2 or 3; or $NR_4R_5$ represents
2-(1,2,3,4-tetrahydroisoquinolinyl), either unsubstituted or mono or disubstituted with halogen, hydroxy, straight or branched chain lower alkyl having 1–6 carbon atoms, or straight or branched chain lower alkoxy having 1–6 carbon atoms; or $NR_4R_5$ represents

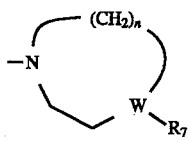

where
W is
N or CH;
$R_7$ is
hydrogen, phenyl, arylalkyl, pyridyl or pyrimidinyl, unsubstituted or mono or disubstituted with halogen, hydroxy, straight or branched chain lower alkyl having 1–6 carbon atoms, or straight or branched chain lower alkoxy having 1–6 carbon atoms; or
W—$R_7$ is
oxygen or sulfur; and
n is
1, 2, or 3.

Preferred compounds of Formula IV are those where W is CH and $R_7$ is an arylalkyl more preferably a benzyl, group.
The invention also provides compounds of formula V:

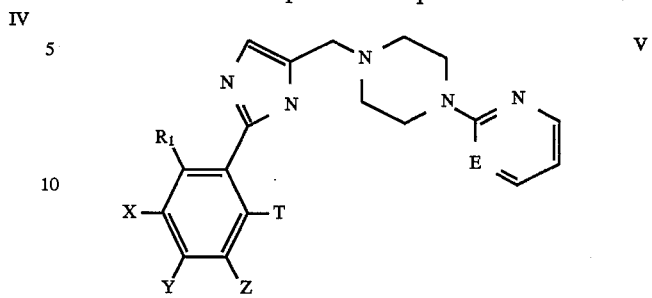

wherein:
$R_1$ and T independently represent hydrogen, halogen, hydroxy, lower alkyl, or lower alkoxy;
X, Y and Z independently represent hydrogen, halogen, hydroxy, lower alkyl, lower alkoxy, or —$SO_2R_6$ where $R_6$ is lower alkyl; and
E is CH or nitrogen.
The invention also provides compounds of formula VI:

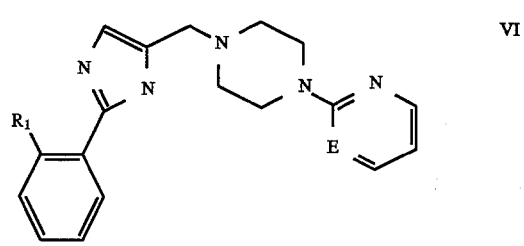

wherein:
$R_1$ represents hydrogen, halogen, hydroxy, lower alkyl, or lower alkoxy; and
E is CH or nitrogen.
The invention provides compounds of formula VII:

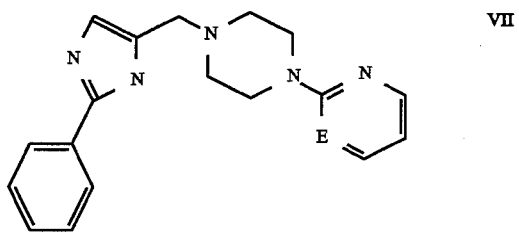

wherein:
E is CH or nitrogen.
The invention also provides compounds of formula VIII:

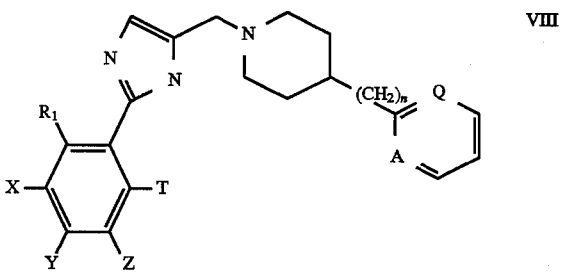

wherein:
$R_1$ and T independently represent hydrogen, halogen, hydroxy, lower alkyl, or lower alkoxy;
X, Y and Z independently represent hydrogen, halogen, hydroxy, lower alkyl, lower alkoxy, or —$SO_2R_6$ where R6 is lower alkyl;

n is 0 or 1; and

A and Q are the same or different and represent CH or nitrogen.

The invention also provides compounds of formula IX:

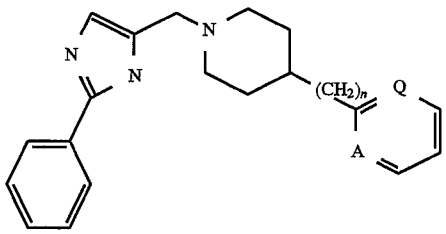

wherein:

n is 0 or 1; and

A and Q are the same or different and represent CH or nitrogen.

The invention also provides compounds of formula X:

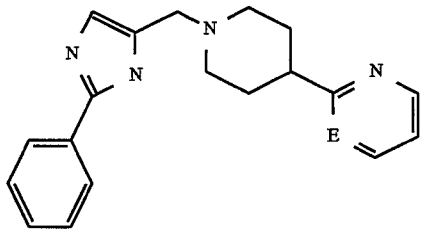

wherein:

E is CH or nitrogen.

The invention also provides compounds of formula XI:

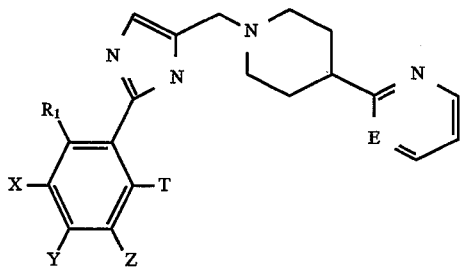

wherein:

$R_1$, T, X, Y and Z independently represent hydrogen or lower alkyl; and E represents CH or nitrogen.

The invention also provides compounds of formula XII:

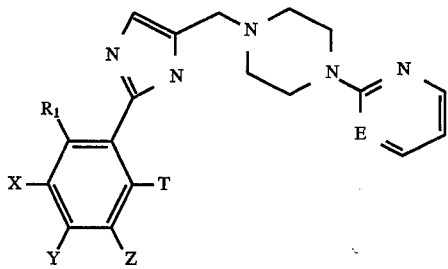

wherein:

$R_1$, T, X, Y and Z independently represent hydrogen or lower alkyl; and E represents CH or nitrogen.

The invention also provides compounds of formula XIII:

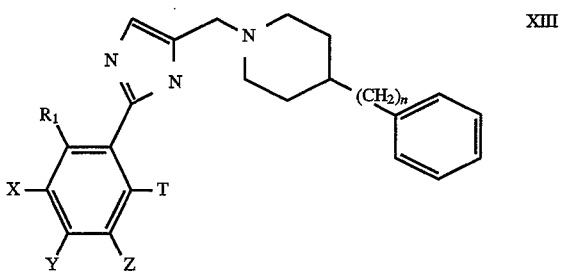

wherein $R_1$ and T independently represent hydrogen, halogen, hydroxy, lower alkyl, or lower alkoxy; and X, Y and Z independently represent hydrogen, halogen, hydroxy, lower alkyl, lower alkoxy, or —$SO_2R_6$ where $R_6$ is lower alkyl.

n is 0 or 1.

The invention also provides compounds of formula XIV:

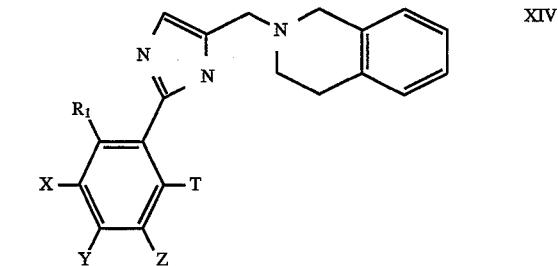

wherein:

$R_1$ and T independently represent hydrogen, halogen, hydroxy, lower alkyl, or lower alkoxy; and X, Y and Z independently represent hydrogen, halogen, hydroxy, lower alkyl, lower alkoxy, or —$SO_2R_6$ where $R_6$ is lower alkyl.

Non-toxic pharmaceutical salts include salts of acids such as hydrochloric, phosphoric, hydrobromic, sulfuric, formic, toluene sulfonic, hydroiodic, acetic and the like. Those skilled in the art will recognize a wide variety of non-toxic pharmaceutically acceptable addition salts.

Representative compounds of the present invention, which are encompassed by Formula I, include, but are not limited to the compounds in FIG. I and their pharmaceutically acceptable salts. The present invention also encompasses the acylated prodrugs of the compounds of Formula I. Those skilled in the art will recognize various synthetic methodologies which may be employed to prepare non-toxic pharmaceutically acceptable addition salts and acylated prodrugs of the compounds encompassed by Formula I.

By "aryl" and "Ar" is meant an aromatic carbocyclic group having a single ring (e.g., phenyl), multiple rings (e.g., biphenyl), or multiple condensed rings in which at least one is aromatic, (e.g., 1,2,3,4-tetrahydronaphthyl, naphthyl, anthryl, or phenanthryl), which can optionally be unsubstituted or substituted with e.g., halogen, lower alkyl, lower alkoxy, lower alkylthio, trifluoromethyl, lower acyloxy, aryl, heteroaryl, and hydroxy.

By "alkyl" and "lower alkyl" is meant straight and branched chain alkyl groups having from 1–6 carbon atoms.

By "lower alkoxy" and "alkoxy" is meant straight and branched chain alkoxy groups having from 1–6 carbon atoms.

By "hydroxy lower alkyl" or "hydroxy alkyl" is meant an alkyl group substituted by at least one hydroxy group.

Preferred hydroxy alkyl groups are straight chain alkyl groups substituted with one hydroxy group at the terminal carbon atom.

By "heteroaryl" is meant 5, 6, or 7 membered aromatic ring systems having at least one hetero atom selected from the group consisting of nitrogen, oxygen and sulfur. Examples of heteroaryl groups are pyridyl, pyrimidinyl, pyrrolo, pyrazolo, pyrazinyl, pyridazinyl, oxazolo, furanyl, quinoline, isoquinoline, thiazole, and thienyl, which can optionally be unsubstituted or substituted with e.g., halogen, lower alkyl, lower alkoxy, lower alkylthio, trifluoromethyl, lower acyloxy, aryl, heteroaryl, and hydroxy.

By "halogen" is meant fluorine, chlorine, bromine and iodine.

By "arylalkyl" is meant the group —R—Ar where Ar is an aryl group and R is a straight or branched chain aliphatic group. Arylalkyl groups may optionally be substituted with, e.g., halogen, lower alkyl, lower alkoxy, lower alkylthio, trifluoromethyl, lower acyloxy, and hydroxy. Preferred arylalkyl groups in the above formulas where W is CH and $R_8$ represents arylalkyl are phenylalkyl groups where the alkyl portion is lower alkyl. A particularly preferred phenylalkyl group is benzyl where the phenyl ring may be substituted with up to three substituents independently selected from hydrogen, halogen, trifluoromethyl, hydroxy, straight or branched chain lower alkyl having 1–6 carbon atoms, or straight or branched chain lower alkoxy having 1–6 carbon atoms.

By "cycloalkyl" is meant cyclic hydrocarbons having from 3–8 carbon atoms. These cyclic hydrocarbon groups may be substituted with up to three substituents independently selected from hydrogen, halogen, trifluoromethyl, cyano, straight or branched chain lower alkyl having 1–6 carbon atoms, hydroxy, straight or branched chain lower alkyl having 1–6 carbon atoms, straight or branched chain lower alkoxy having 1–6 carbon atoms, or $SO_2R_9$ where $R_9$ is $NH_2$ or $NHCH_3$.

The pharmaceutical utility of compounds of this invention are indicated by the following assays for dopamine receptor subtype affinity.

Assay for D2 and D3 receptor binding activity

Striatial tissue is dissected from adult male Sprague Dawley rats or BHK 293 cells are harvested containing recombinantly produced D2 or D3 receptors. The sample is homogenized in 100 volumes (w/vol) of 0.05M Tris HCl buffer at 4° C. and pH 7.4. The sample is then centrifuged at 30,000 ×g and resuspended and rehomogenized. The sample is then centrifuged as described and the final tissue sample is frozen until use. The tissue is resuspended 1:20 (wt/vol) in 0.05M Tris HCl buffer containing 100 mM NaCl.

Incubations are carried out at 48° C. and contain 0.5 ml of tissue sample, 0.15 nM 3H-raclopride and the compound of interest in a total incubation of 1.0 ml. Nonspecific binding is defined as that binding found in the presence of 10-4M dopamine; without further additions, nonspecific binding is less than 20% of total binding. The binding characteristics of examples of this patent are shown in Table 1 for Rat Striatal Homogenates.

TABLE I

| Compound Number[1] | $IC_{50}$(uM) |
|---|---|
| 1 | 0.900 |
| 8 | 0.011 |
| 16 | 0.014 |
| 19 | 0.100 |

TABLE I-continued

| Compound Number[1] | $IC_{50}$(uM) |
|---|---|
| 21 | 0.018 |
| 24 | 0.620 |
| 26 | 0.200 |

[1]Compound numbers relate to compounds shown in FIG. I.

Assay for D4 receptor binding activity

Clonal cell lines expressing the human dopamine D4 receptor subtype were harvested in PBS and the cells centrifuged and the pellets stored at −80° C. until used in the binding assay. The pellets were resuspended and the cells; lysed at 4 C in 50 mM Tris pH 7.4 buffer containing 120mM Nacl, 1 mM EDTA and 5 mM $MgCl_2$. The homogenate is centrifuged at 48000×g for 10 minutes at 4 C.

The resulting pellet is resuspended in fresh buffer and centrifuged again, After resuspension of the pellet in fresh buffer at 1.00 ul aliquot is removed for protein determination. The remaining homogenate is centrifuged as above, the supernatant removed and the pellet stored at 4 C until needed at which time it is resuspended to a final concentration of 625 ug/ml(250 ug per sample) with 50 mM Tris buffer (pH 7.4) and 120 mM NaCl just prior to use. Incubations were carried out for 60 minutes at 25 C in the presence of 0.1 nM [$^3$H]YM-09151-2. The incubation was terminated by rapid filtration through Whatman GF/C filters and rinsed with 2×4 ml washes of chilled 50 mM Tris (pH 7.4) and 120 mM NaCl. Non-specific binding was determined with 1 uM spiperone and radioactivity determined by counting in an LKB beta counter. Binding parameters were determined by non-linear least squares regression analysis, from which the inhibition constant Ki could be calculated for each test compound. The binding characteristics of some examples of this patent are shown in Table 2 for the dopamine D4 binding assay. In general, compounds of the accompanying Examples were tested in the above assay, and all were found to possess a Ki value for the displacement of [3H]YM-09151-2 from the human dopamine D4 receptor subtype of below 500 nM. Some specific data is indicated in Table 2

TABLE 2

| Compound Number[1] | Ki(uM) |
|---|---|
| 19 | 0.001 |
| 20 | 0.014 |
| 22 | 0.048 |
| 23 | 0.003 |
| 24 | 0.001 |
| 25 | 0.002 |
| 43 | 0.014 |
| 45 | 0.005 |
| 47 | 0.053 |
| 50 | 0.005 |
| 52 | 0.002 |
| 55 | 0.500 |
| 56 | 0.450 |
| 58 | 0.003 |
| 60 | 0.015. |
| 61 | 0.013 |
| 65 | 0.013 |

[1]Compound numbers relate to compounds shown in FIG. I.

Compounds 8, 16, 19, 21, 23, 24, 25 and 52 are particularly preferred embodiments of the present invention because of their potency in binding to dopamine receptor subtypes.

The compounds of general formula I may be administered orally, topically, parenterally, by inhalation or spray or rectally in dosage unit formulations containing conventional non-toxic pharmaceutically acceptable carriers, adjuvants and vehicles. The term parenteral as used herein includes subcutaneous injections, intravenous, intramuscular, intrasternal injection or infusion techniques. In addition, there is provided a pharmaceutical formulation comprising a compound of general formula I and a pharmaceutically acceptable carrier. One or more compounds of general formula I may be present in association with one or more non-toxic pharmaceutically acceptable carriers and/or diluents and/or adjuvants and if desired other active ingredients. The pharmaceutical compositions containing compounds of general formula I may be in a form suitable for oral use, for example, as tablets, troches, lozenges, aqueous or oily suspensions, dispersible powders or granules, emulsion, hard or soft capsules, or syrups or elixirs.

Compositions intended for oral use may be prepared according to any method known to the art for the manufacture of pharmaceutical compositions and such compositions may contain one or more agents selected from the group consisting of sweetening agents, flavoring agents coloring agents and preserving agents in order to provide pharmaceutically elegant and palatable preparations. Tablets contain the active ingredient in admixture with non-toxic pharmaceutically acceptable excipients which are suitable for the manufacture of tablets. These excipients may be for example, inert diluents, such as calcium carbonate, sodium carbonate, lactose, calcium phosphate or sodium phosphate; granulating and disintegrating agents, for example, corn starch, or alginic acid; binding agents, for example starch, gelatin or acacia, and lubricating agents, for example magnesium stearate, stearic acid or talc. The tablets may be uncoated or they may be coated by known techniques to delay disintegration and absorption in the gastrointestinal tract and thereby provide a sustained action over a longer period. For example, a time delay material such as glyceryl monosterate or glyceryl distearate may be employed.

Formulations for oral use may also be presented as hard gelatin capsules wherein the active ingredient is mixed with an inert solid diluent, for example, calcium carbonate, calcium phosphate or kaolin, or as soft gelatin capsules wherein the active ingredient is mixed with water or an oil medium, for example peanut oil, liquid paraffin or olive oil.

Aqueous suspensions contain the active materials in admixture with the manufacture of aqueous suspensions. Such excipients are suspending gents, for example sodium carboxymethylcellulose, methylcellulose, hydropropylmethylcellulose, sodium alginate, polyvinylpyrrolidone, gum tragacanth and gum acacia; dispersing or wetting agents may be a naturally-occurring phosphatide, for example, lecithin, or condensation products of an alkylene oxide with fatty acids, for example polyoxyethylene stearate, or condensation products of ethylene oxide with long chain aliphatic alcohols, for example heptadecaethyleneoxycetanol, or condensation products of ethylene oxide with partial esters derived from fatty acids and a hexitol such as polyoxyethylene sorbitol monooleate, or condensation products of ethylene oxide with partial esters derived from fatty acids and hexitol anhydrides, for example polyethylene sorbitan monooleate. The aqueous suspensions may also contain one or more preservatives, for example ethyl, or n-propyl p-hydroxybenzoate, one or more coloring agents, one or more flavoring agents, and one or more sweetening agents, such as sucrose or saccharin.

Oily suspensions may be formulated by suspending the active ingredients in a vegetable oil, for example arachis oil, olive oil, sesame oil or coconut oil, or in a mineral oil such as liquid paraffin. The oily suspensions may contain a thickening agent, for example beeswax, hard paraffin or cetyl alcohol. Sweetening agents such as those set forth above, and flavoring agents may be added to provide palatable oral preparations. These compositions may be preserved by the addition of an anti-oxidant such as ascorbic acid.

Dispersible powders and granules suitable for preparation of an aqueous suspension by the addition of water provoke the active ingredient in admixture with a dispersing or wetting agent, suspending agent and one or more preservatives. Suitable dispersing or wetting agents and suspending agents are exemplified by those already mentioned above. Additional excipients, for example sweetening, flavoring and coloring agents, may also be present.

Pharmaceutical compositions of the invention may also be in the form of oil-in-water emulsions. The oily phase may be a vegetable oil, for example olive oil or arachis oil, or a mineral oil, for example liquid paraffin or mixtures of these. Suitable emulsifying agents may be naturally- occurring gums, for example gum acacia or gum tragacanth, naturally-occurring phosphatides, for example soy bean, lecithin, and esters or partial esters derived from fatty acids and hexitol, anhydrides, for example sorbitan monoleate, and condensation products of the said partial esters with ethylene oxide, for example polyoxyethylene sorbitan monoleate. The emulsions may also contain sweetening and flavoring agents.

Syrups and elixirs may be formulated with sweetening agents, for example glycerol, propylene glycol, sorbitor or sucrose. Such formulations may also contain a demulcent, a preservative and flavoring and coloring agents. The pharmaceutical compositions may be in the form of a sterile injectable aqueous or oleaginous suspension. This suspension may be formulated according to the known art using those suitable dispersing or wetting agents and suspending agents which have been mentioned above. The sterile injectable preparation may also be sterile injectable solution or suspension in a non-toxic parentally acceptable diluent or solvent, for example as a solution in 1,3-butanediol. Among the acceptable vehicles and solvents that may be employed are water. Ringer's solution and isotonic sodium chloride solution. In addition, sterile, fixed oils are conventionally employed as a solvent or suspending medium. For this purpose any bland fixed oil may be employed including synthetic mono-or diglycerides. In addition, fatty acids such as oleic acid find use in the preparation of injectables.

The compounds of general formula I may also be administered in the form of suppositories for rectal administration of the drug. These compositions can be prepared by mixing the drug with a suitable non-irritating excipient which is solid at ordinary temperatures but liquid at the rectal temperature and will therefore melt in the rectum to release the drug. Such materials are cocoa butter and polyethylene glycols.

Compounds of general formula I may be administered parenterally in a sterile medium. The drug, depending on the vehicle and concentration used, can either be suspended or dissolved in the vehicle. Advantageously, adjuvants such as local anaesthetics, preservatives and buffering agents can be dissolved in the vehicle.

Dosage levels of the order of from about 0.1 mg to about 140 mg per kilogram of body weight per day are useful in the treatment of the above-indicated conditions (about 0.5 mg to about 7 g per patient per day). The amount of active ingredient that may be combined with the carrier materials to produce a single dosage form will vary depending upon the host treated and the particular mode of administration.

Dosage unit forms will generally contain between from about 1 mg to about 500 mg of an active ingredient It will be understood, however, that the specific dose level for any particular patient will depend upon a variety of factors including the activity of the specific compound employed, the age, body weight, general health, sex, diet, time of administration, route of administration, and rate of excretion, drug combination and the severity of the particular disease undergoing therapy.

An illustration of the preparation of compounds of the present invention is given in Scheme I. Those having skill in the art will recognize that the starting materials may be varied and additional steps employed to produce compounds encompassed by the present invention.

$R_4$ and $R_5$ are the same or different and represent hydrogen, straight or branched chain lower alkyl having 1–6 carbon atoms, aryl straight or branched chain lower alkyl having 1–6 carbon atoms or $R_2$ and $R_5$ together may represent —$(CH_2)_{n3}$— where $n_3$ is 2 or 3; or $NR_4R_5$ represents 2-(1,2,3,4-tetrahydroisoquinolinyl), either unsubstituted or mono or disubstituted with halogen, hydroxy, straight or branched chain lower alkyl having 1–6 carbon atoms, or straight or branched chain lower alkoxy having 1–6 carbon atoms; or

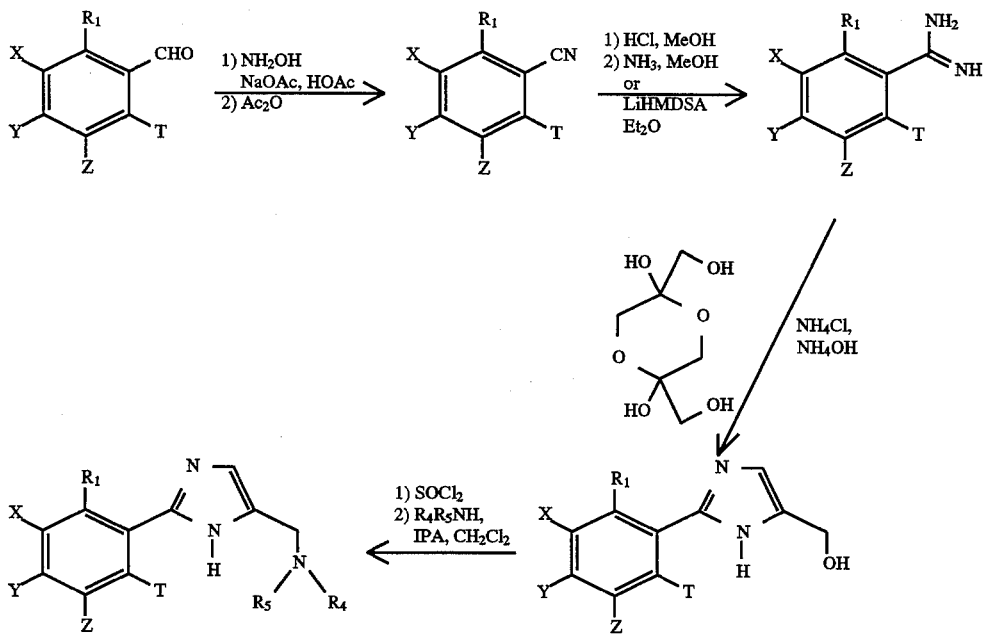

Scheme 1 where $R_1$ and T are the same or different and represent hydrogen, halogen, hydroxy, straight or branched chain lower alkyl having 1–6 carbon atoms, or straight or branched chain lower alkoxy having 1–6 carbon atoms;

$R_2$ is hydrogen or, straight or branched chain lower alkyl having 1–6 carbon atoms, or $R_1$ and $R_2$ together may represent —$(CH_2)_{n1}$ where $n_1$ is 1, 2, or 3;

X and Z are the same or different and represent hydrogen, halogen, hydroxy, straight or branched chain lower alkyl having 1–6 carbon atoms, straight or branched chain lower alkoxy having 1–6 carbon atoms or $SO_2R_6$ where $R_6$ is straight or branched chain lower alkyl having 1–6 carbon atoms;

Y is hydrogen, amino, halogen, or straight or branched chain lower alkyl having 1–6 carbon atoms;

$R_3$ is hydrogen or, straight or branched chain lower alkyl having 1–6 carbon atoms, or $R_3$ and $R_4$ together may represent —$(CH_2)_{n2}$— where $n_2$ is 3 or 4;

$NR_4R_5$ represents

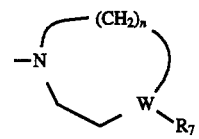

where

W is

N or CH;

$R_7$ is hydrogen, phenyl, arylalkyl, pyridyl or pyrimidinyl, unsubstitute or mono or disubstituted with halogen, hydroxy, straight or branched chain lower alkyl having 1–6 carbon atoms, or straight or branched chain lower alkoxy having 1–6 carbon atoms; or W—$R_7$ is oxygen or sulfur; and n is 1, 2, or 3.

Alternative routes for the preparation of compounds of the invention are depicted in Schemes 2 and 3, below. The substituents on the starting materials and reagents carry the definitions as for formula I above.

Scheme 2

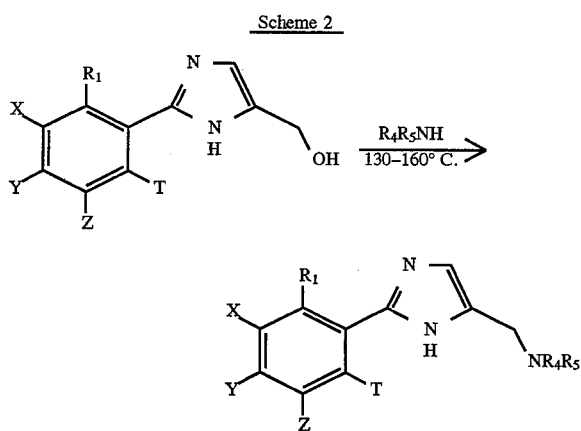

Scheme 3

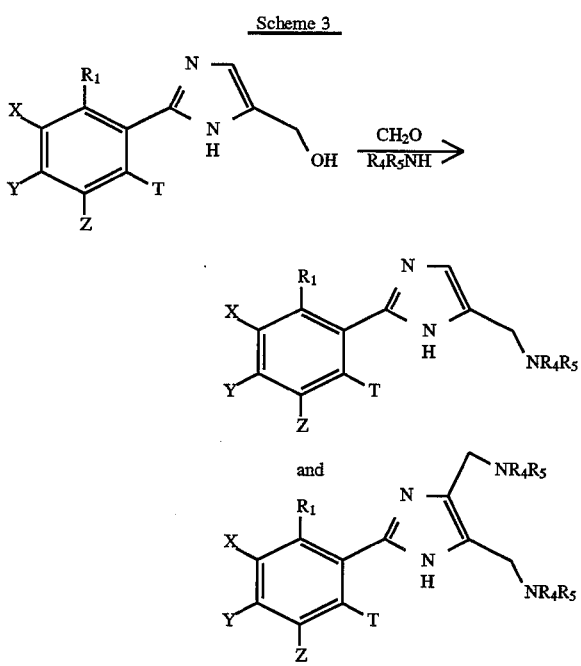

The invention is illustrated further by the following examples which are not to be construed as limiting the invention in scope or spirit to the specific procedures and compounds described in them.

EXAMPLE I

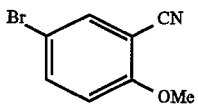

A mixture of 5-Bromo-o-anisaldehyde (6.45 g), hydroxylamine hydrochloride (2.2 g), sodium acetate (4.1 g) and acedc acid (20 mL) was heated at 100° C. with stirring for 1 h. Acetic anhydride was added (20 mL) and the mixture was refluxed for 8 h. The reaction mixture was poured onto ice water and the mixture was made basic by the careful addition of 50% sodium hydroxide. The product was extracted with ether, the ether extracts were dried over magnesium sulfate and the solvent was removed in vacuo. The residue was crystallized from ether/hexane to afford 5-Bromo-2-methoxy-benzonitrile.

EXAMPLE II

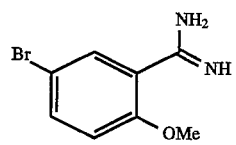

A mixture of 5-Bromo-2-methoxy-benzonitrile (4.0 g), 3A molecular sieves (5 g) and anhydrous methanol (60 mL) was saturated with HCl gas at romm temperature and allowed to stand at room temperate for 24 h. The solvent was remove in vacuo and the residue taken up in 75 mL of anhydrous methanol and saturated with ammonia gas at room temperature. The reaction mixture was then heated at 80° C. for 4 h in a sealed tube. The solvent was removed in vacuo, the reaction mixture was diluted with 3N HCl and washed with ethyl acetate to remove unreacted nitrile. The aqueous layer was made basic with 50% NaOH and the product was extracted three times with 10% methanol in methylene chloride. The combined organic extracts were dried over magnesium sulphate and the sovents removed in vacuo to afford 5-Bromo-2-methoxy-benzamidine as a glassy solid.

EXAMPLE III

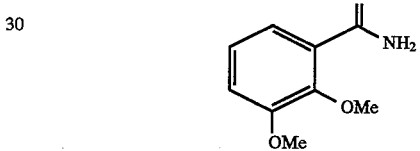

To a solution of 1,1,1,3,3,3-hexamethylsisilazane (20 g) in dry ether (150 mL) was added 2.4M n-butyllithium in hexane (5 mL). After 10 rain at room temperature, 2,3-Dimethoxybenzonitrile (16.3 g) was added in one portion and the mixture was kept at room temperature for 16 h. The reaction mixture was the poured onto excess 3N HCl. The aqueous layer was separated, basified with 50% NaOH and the product was extracted three times with 10% methanol in methylene chloride. The combined organic extracts were dried over magnesium sulfate and the solvents removed in vacuo to afford 2,3-Dimethoxy-benzamidine as a glassy solid.

EXAMPLE IV

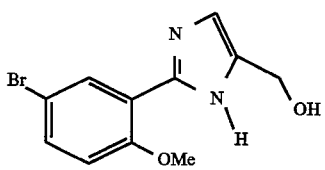

A mixture of 5-Bromo-2-methoxy-benzamidine (1.5 g), 1,3-dihydroxy-acetone dimer (1.0 g), ammonium chloride (1.3 g), tetrahydrofuran (3 mL) and concentrated aqueous ammonium hydroxide (10 mL) was heated at 90° C. for 3 h. The reaction mixture was chilled on ice and the precipitated product was collected and recrystallized from methanol to afford 2-(5-Bromo-2-methoxyphenyl)-5-hydroxymethyl-imidazole as a yellow solid.

EXAMPLE V

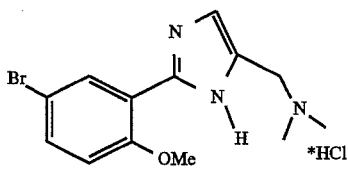

(Compound 1)

A mixture of 2-(5-Bromo-2-methoxyphenyl)-5-hydroxymethyl-imidazole (500 mg) and thionyl chloride (1.5 mL) was heated at 80° C. for 1 h. Ether (15 mL) was added and the resulting solid was collected and washed with ether. This solid was added in one portion to a mixture of dimethylamine (3 mL), isopropanol (15 mL) and methylene chloride (30 mL) and the mixture was stirred for 20 min. The solvents were removed in vacuo and the residue was dissolved in 2N HCl and washed two times with ethyl acetate. The aqueous layer was made basic with 50% NaOH and the product was extracted with methylene chloride. The organic extracts were dried over magnesium sulfate, the solvents removed in vacuo, and the residue was treated with ethanolic HCl/ether to afford 2-(5-Bromo-2-methoxyphenyl)-4(5)-[(N,N-dimethyl)aminomethyl]-imidazole dihydrochloride (Compound 1), m.p. 242°–243° C.

EXAMPLE VI

The following compounds were prepared essentially according to the procedure described in Examples I–V:

(a) 2-Phenyl-4(5)-[(N,N-dimethyl)aminomethyl]-imidazole dihydrochlofide (Compound 2), m.p. 259°–260° C.

(b) 2-Phenyl-4(5)-(piperidinomethyl)-imidazole dihydrochloride (Compound 3), m.p. 245°–247° C.

(c) 2-Phenyl-4(5)-[(N-methyl-N-benzyl)aminomethyl]-imidazole dihydrochloride (Compound 4), m.p. 239°–240° C.

(d) 2-(2-Methoxyphenyl)-4(5)-[(N,N-dimethyl)aminomethyl]-imidazole dihydrochloride (Compound 5) melting at 208°–211° C.

(e) 2-(3-Methoxyphenyl)-4(5)-[(N-methyl-N-benzyl)aminomethyl]-imidazole dihydrochloride (Compound 6), m.p. 115°–117° C.

(f) 2-(2,3-Dimethoxyphenyl)-4(5)-[(N,N-dimethyl)aminomethyl]-imidazole dihydrochloride (Compound 7), m.p. 220°–221° C.

(g) 2-(2,3-Dimethoxyphenyl)-4(5)-[(N-methyl-N-benzyl)aminomethyl]-imidazole dihydrochloride (Compound 8), m.p. 200°–202° C.

(h) 2-(3-Methoxyphenyl)-4(5)-[(N,N-diethyl)aminomethyl]-imidazole dihydrochloride (Compound 9), m.p. 213°–214° C.

(i) 2-(3-Fluorophenyl)-4(5)-[(N,N-dimethyl)aminomethyl]-imidazole dihydrochloride (Compound 10), m.p. 211°–214° C.

(j) 2-(2-Fluorophenyl)-4(5)-[(N-methyl-N-benzyl)aminomethyl]-imidazole dihydrochloride (Compound 11), m.p. 241°–244° C.

(k) 2-(3-Methylphenyl)-4(5)-[(N,N-dimethyl)aminomethyl]-imidazole dihydrochloride (Compound 12), m.p. 231°–234° C.

(l) 2-(2-Fluorophenyl)-4(5)-[(N,N-dimethyl)aminomethyl]-imidazole dihydrochloride (Compound 13), m.p. 237°–239° C.

(m) 2-(4-Fluorophenyl)-4(5)-[(N-methyl-N-benzyl)aminomethyl]-imidazole dihydrochloride (Compound 14), m.p. 237°–239° C.

(n) 2-(2-Methoxyphenyl)-4(5)-[(N-methyl-N-benzyl)aminomethyl]-imidazole dihydrochloride (Compound 15), m.p. 239°–241° C.

(o) 2-(5-Bromo-2,3-dimethoxyphenyl)-4(5)-[(N,N-dimethyl)aminomethyl]-imidazole dihydrochloride (Compound 16), m.p. 194°–194° C.

(p) 2-(5-Bromo-2-methoxyphenyl)-4(5)-[(N-methyl-N-benzyl)aminomethyl]-imidazole dihydrochloride (Compound 17), m.p. 242°–243° C.

(q) 2-(5-Bromo-2,3-dimethoxyphenyl)-4(5)-[(N-methyl-N-benzyl)aminomethyl]-imidazole dihydrochloride (Compound 18).

EXAMPLE VII

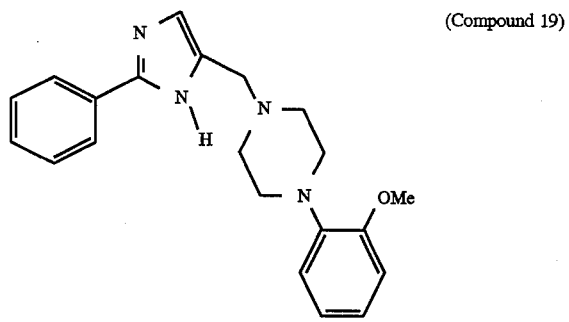

(Compound 19)

A mixture of 2-Phenyl-5-hydroxymethyl-imidazole (350 mg) and thionyl chloride (1 mL) was heated at 80° C. for 1 h. The excess thionyl chloride was removed in vacuo and the residue was dissolved in 20 mL of methylene chloride. This solution was added to a mixture of triethylamine (1 mL) and 1-(2-methoxyphenyl)-piperazine (410 mg) in methylene chloride (20 mL) and the mixture was stirred for 20 min. The solvents were removed in vacuo and the residue was dissolved in 2N HCl and washed two times with ethyl acetate. The aqueous layer was made basic with 50% NaOH and the product was extracted with methylene chloride. The organic extracts were dried over magnesium sulfate, the solvents removed in vacuo, and the residue was crystallized from ethyl acetate to afford 2-Phenyl-4(5)-[(4-(2-methoxyphenyl)-piperazin-1-yl)methyl]-imidazole (Compound 19), m.p. 105°–107° C.

EXAMPLE VIII

The following compounds were prepared essentially according to the procedure described in Example VII:

(a) 2-(4-Fluorophenyl)-4(5)-[(4-(2-methoxyphenyl)-piperazin-1-yl)-methyl]-imidazole (Compound 20), m.p. 95°–97° C.

(b) 2-(2,3-Dimethoxyphenyl)-4(5)-[(4-(2-methoxyphenyl)-piperazin-1-yl)-methyl]-imidazole dihydrochloride (Compound 21), m.p. 217°–218° C.

(c) 2-(3-Chlorophenyl)-4(5)-[(4-(2-methoxyphenyl)-piperazin-1-yl)-methyl]-imidazole dihydrochloride (Compound 22), m.p. 198°–199° C.

(d) 2-Phenyl-4(5)-[(4-(2-pyrimidinyl)-piperazin-1-yl)-methyl]-imidazole dihydrochloride (Compound 23), m.p. 246°–248° C.

(e) 2-Phenyl-4(5)-[(4-(2-pyridyl)-piperazin-1-yl)-methyl]-imidazole dihydrochloride (Compound 24), m.p. 176°–177° C.

(f) 2-Phenyl-4(5)-[(4-benzyl-piperidin-1-yl)-methyl]-imidazole dihydrochloride (Compound 25), m.p. 234°–236° C.

(g) 2-Phenyl-4(5)-[(4-phenyl-piperidin-1-yl)-methyl]-imidazole dihydrochloride (Compound 26), m.p. 238°–240° C.

(h) 2-Phenyl-4(5)-[(1,2,3,4-tetrahydroisoquinolin)-2-yl-methyl]-imidazole dihydrochloride (Compound 27).

(i) 2-phenyl-4(5)-[(4-(2-pyrimidinyl)piperazin-1-yl)methyl]-imidazole (Compound 23A).

(j) 2-phenyl-4(5)-[(4-(2-pyrimidinyl)piperazin-1-yl)methyl]-imidazole dimaleate salt (Compound 23B), m.p. 176°–178° C.

EXAMPLE IX

The following compounds were prepared essentially according to the procedures described in Examples I–VII:

(a) 2-(2,3-Dimethoxyphenyl)-4(5)-[(1,2,3,4-tetrahydroisoquinolin)-2-yl-methyl]-imidazole dihydrochloride (Compound 28), m.p. 205°–207° C.

(b) 2-(4-Methoxyphenyl)-4(5)-[(N-methyl-N-benzyl)aminomethyl]-imidazole dihydrochloride (Compound 29).

(c) 2-(3,4-Dimethoxyphenyl)-4(5)-[(N-methyl-N-benzyl)aminomethyl]-imidazole dihydrochloride (Compound 30).

(d) 2-(3-Methoxyphenyl)-4(5)-[(N-methyl)aminomethyl]-imidazole dihydrochloride (Compound 31).

(e) 2-(5Chloro-2-methoxyphenyl)-4(5)-[(N-methyl-N-benzyl)aminomethyl]-imidazole (Compound 32), m.p. 88°–89° C.

(f) 2-(5-Chloro-2-methoxyphenyl)-4(5)-[(N,N-dimethyl)aminomethyl]-imidazole dihydrochloride (Compound 33), m.p. 231°–233° C.

(g) 2-(5-Chloro-2-methoxyphenyl)-4(5)-[(N-methyl)aminomethyl]-imidazole dihydrochloride (Compound 34), m.p. 225°–227° C.

(h) 2-(5-Chloro-2-methoxyphenyl)-4(5)-[(N-benzyl)aminomethyl]-imidazole dihydrochloride (Compound 35), m.p. 184°–186° C.

(i) 2-(5-Chloro-2-benzyloxyphenyl)-4(5)-[(,N-methyl-N-benzyl)aminomethyl]-imidazole dihydrochloride (Compound 36), m.p. 118°–123° C.

(j) 2-(2-Benzyloxyphenyl)-4(5)-[(N-methyl-N-benzyl)aminomethyl]-imidazole dihydrochloride (Compound 37), m.p. 199°–200° C.

(l) 2-(3-Ethylphenyl)-4(5)-[(N-methyl-N-benzyl)aminomethyl]-imidazole dihydrochloride (Compound 38), m.p. 234°–235° C.

(m) 2-(5-Chloro-2-methoxyphenyl)-4(5)-[(N-methyl-N-(-4-chlorobenzyl))aminomethyl]-imidazole dihydrochloride (Compound 39), m.p. 186°–188° C.

(n) 2-(5-hydroxyphenyl)-4(5)-[(N-methyl-N-benzyl)aminomethyl]-imidazole dihydrochloride (Compound 40), m.p. 227°–228° C.

(o) 2-(5-Bromo-2-benzyloxyphenyl)-4(5)-[(N-methyl-N-benzyl)aminomethyl]-imidazole dihydrochloride (Compound 41).

(p) 2-(5-Ethyl-2-methoxyphenyl)-4(5)-[(N-methyl-N-benzyl)aminomethyl]-imidazole dihydrochloride (Compound 42), m.p. 114°–115° C.

(q) 2-(5-Chloro-2-methoxyphenyl)-4(5)-[(4-(2-methoxyphenyl)-piperazin-1-yl)-methyl]-imidazole dihydrochloride (Compound 43) melting at 138°–143° C.

(r) 2-(5-Chloro-2-methoxyphenyl)-4(5)-[(4-phenyl-piperidin-1-yl)-methyl]-imidazole dihydrochloride (Compound 44), m.p. 138°–143° C.

(s) 2-Phenyl-4(5)-[(4-phenyl-piperazin-1-yl-) methyl] imidazole (Compound 45), m.p. 189°–191° C.

(t) 2-(4-Fluorophenyl)-4(5)[(4-phenyl-piperidin-1-yl)-methyl]-imidazole dihydrochloride (Compound 46), m.p. 260°–264° C. (dec)

(u) 2-(4-Methoxyphenyl)-4(5)[(4-phenyl-piperidin-1 -yl)-methyl]-imidazole dihydrochloride (Compound 47), m.p. 196°–199° C.

(v) 2-Phenyl-4(5)-[(4-(3-trifluoromethylphenyl) - piperazin-1-yl-)methyl]imidazole (Compound 48), m.p. 182°–184° C.

(w) 2-(2-Methoxyphenyl)-4(5)[(4-phenyl-piperidin-1-yl)-methyl]-imidazole dihydrochloride (Compound 49).

(x) 2-(3-Methoxyphenyl)-4(5)[(4-phenyl-piperidin-1 -yl)-methyl]-imidazole dihydrochloride (Compound 50), m.p. 114°–117° C.

(y) 2-(3-Fluorophenyl)-4(5)[(4-phenyl-piperidin-1 -yl)-methyl]-imidazole (Compound 51), m.p. 110°–112° C.

(z) 2-(2-Fluorophenyl)-4(5)[(4-phenyl-piperidin-1-yl)-methyl]-imidazole dimaleate (Compound 52), m.p. 142°–144° C.

(aa) 2-(2-Methylphenyl)-4(5)-[(4-benzyl-piperidin-1-yl)-methyl]-imidazole dihydrochloride (Compound 53), m.p. 242°–244° C.

(ab) 2-(5-Ethyl-2-methoxyphenyl-4(5)-[(4-phenyl-piperidin-1 -yl)-methyl]-imidazole dihydrochloride (Compound 54), m.p. 76°–78° C.

(ac) 2-(5-Ethyl-2-methoxyphenyl-4(5)-[(4-(2-methoxyphenyl)-piperazin-1-yl)-methyl]- imidazole dihydrochloride (Compound 55), m.p. 61°–64° C.

(ad) 2-Phenyl-4(5)-[(4(4-fluorophenyl)- piperazin-1-yl-) methyl]imidazole dihydrochloride (Compound 56), m.p. 64°–68° C.

(ae) 2-(5-Ethyyl-2-methoxyphenyl4(5)[(4-(2pyrimidinyl)-piperazin-1yl)-methyl]-imidazole dihydrochloride (Compound 57) m.p. 75°–78° C.

(af) 2-Phenyl-4(5)-[(4(5-fluoro-2-pyrimidinyl)-piperazin-1-yl)-methyl]imidazole dihydrochloride (Compound 58), m.p. 188°–190° C.

(ag) 2-(4-Fluorophenyl)-4(5)-[(4-(2-pyrimidinyl)-piperazin-1-yl)-methyl]-imidazole dihydrochloride (Compound 59) m.p. 181°–184° C.

(ah) 2-Phenyl-4(5)-[(4(5-chloro-2-methylphenyl)-piperazin-1-yl-)-methyl]imidazole dihydrochloride (Compound 60), m.p. 142°–145° C.

(ai) 2-Phenyl-4(5)-[(4(3,4-dichlorophenyl)-piperazin-1-yl-)methyl]imidazole (Compound 61), m.p. 179°–181° C.

(aj) 2-Phenyl-4(5)-[(4(4-fluorophenyl)-piperidin-1-yl) methyl]imidazole dimaleate(Compound 62), m.p. 148°–149° C.

(ak) 2-(3-Fluorophenyl)-4(5)-[(4-benzyl-piperidin-1-yl)-methyl]-imidazole dimaleate (Compound 63), m.p. 148°–149° C.

(al) 2-(4-Fluorophenyl)-4(5)-[(4-benzyl-piperidin-1-yl)-methyl]-imidazole dihydrochloride (Compound 64), m.p. 254°–256° C.

(am) 2-Phenyl-4(5)-[(4-(4-fluorobenzyl)-piperidin-1-yl)-methyl]-imidazole dihydrochloride (Compound 65), m.p.

(an) 2-(2-Fluorophenyl)-4(5)-[(4-(2-pyrimidinyl)-piperazin-1-yl)-methyl]-imidazole (Compound 66) m.p. 159°–161° C.

(ao) 2-(4-Methylphenyl)-4(5)-[(4-(2-pyrimidinyl)-piperazin-1-yl)-methyl]-imidazole (Compound 67) m.p. 176°–179° C.

(ap) 2-(2-Fluorophenyl)-4(5)-[(4-benzyl-piperidin-1-yl)-methyl]-imidazole dimaleate (Compound 68), m.p. 113°–115° C.

(aq) 2-(4-Chlorophenyl)-4(5)-[(4-(2-pyridyl)-piperazin-1-yl)-methyl]-imidazole (Compound 69), m.p. 176°–177° C.

(ar) 2-Phenyl-4(5)-[(4-(5-fluoro-2-pyrimidinyl)-piperazin-1-yl)-methyl]-imidazole dimaleate (Compound 70) m.p. 185°–186° C.

(as) 2-(2-Fluorophenyl)-4(5)-[(4-(5-fluoro-2-pyrimidinyl)-piperazin-1-yl)-methyl]-imidazole dimaleate (Compound 71) m.p. 172°–173° C.

(at) 2-(4-Fluorophenyl-4(5)-[(4-(5fluoro-2-pyrimidinyl)-piperazin-1-yl)-methyl]-imidazole dimaleate (Compound 72), m.p. 183°–184° C.

(au) 2-(2,3-Dimethoxyphenyl)-4(5)-[(4(2-methoxyphenyl)-piperidin-1-yl)-methyl]-imidazole dihydrochloride (Compound 72A).

(ax) 2-phenyl-4(5)-[(4-(2-pyridyl)-piperidin-1-yl)-methyl]-imidazole dihydrochloride (Compound 72B).

EXAMPLE X

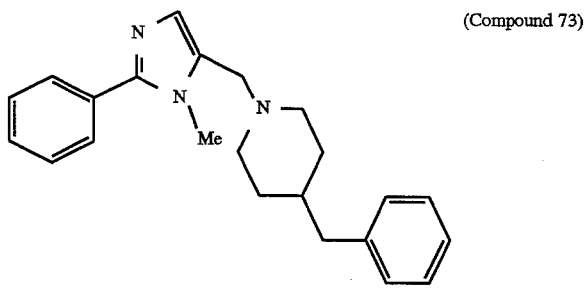

(Compound 73)

A solution of 40 mL tetrahydro furan containing 1.0 g of 2-phenylimidazole was cooled to 0° C. and 4 mL of 2M lithium diisopropylamide was added dropwise which resulted in the formation of a white suspension. The mixture was stirred for 10 min at 0 C and then 0.7 mL of dimethyl sulfate was added/The reaction was allowed to stir at room temperaturee for an additional 30 min by which time the solution became homogeneous. Aqueous ammonium chloride was added and the tetrahydrofuran was removed by evaporation under reduced pressure. The aqueous phase was extracted with 2×100 mL aliquots of clichloromethane. The combined organic extracts were washed with dilute ammonium hydroxide and brine. The combined organic extracts were dried over anhydrous sodium sulfate and concentrated under reduced pressure to yield 1 g of 1-methyl-2-phenylimidazole which was used in the next step without further purification or characterization.

To a solution of 1 g of 1 methyl-2-phenylimidazole in 10 mL acetic acid were added 0.4 mL of 37% aqueous formaldehyde and 1.2 mL of 4-benzylpiperidine. The reaction mixture was heated at 100 C for 10 hours and the acetic acid then removed by evaporated under reduced pressure. The residue was dissolved in water and made alkaline with 5% sodium hydroxide and extracted with 2×100 mL of dichloromethane. The combined extracts were dried over anhydrous sodium sulfate and concentrated to small volume under reduced pressure and the 1 Methyl-2-phenyl-5-[(4-benzyl-piperidin-1-yl)methyl]-imidazole.

The following compounds were prepared essentially according to the procedure described in Example X utilizing 2-phenyl-4(5)-[(4-(2-pyrimidinyl)piperazin-1-yl)methylimidazole (Compound 22) as the starting material. The resulting isomers were separated by chromatography on silica gel using ethyl acetate as eluant.

a) 1 Methyl-2-phenyl-4-[(4-(2-pyrimidinyl)piperazin-1-yl)methyl]-imidazole (Compound 74)

b) 1 Methyl-2-phenyl-5-[(4-(2-pyrimidinyl)piperazin-1-yl)methyl]-imidazole (Compound 75)

EXAMPLE XI

The following compounds were assayed for D2, D3, and D4 receptor binding activity using the assays described above.

| | Receptor Binding Activity (Ki.nM) | | |
|---|---|---|---|
| | Dopamine Receptor | | |
| Compound No. | D2 | D3 | D4 |
| 45 | 239 | 169 | 5 |
| 23 | 1033 | 8200 | 2.7 |
| 24 | 1029 | 123 | 0.85 |

EXAMPLE XII

SUMMARY

The effects of 2-phenyl-4(5)-[(4-(2-pyrimidyl)-piperazin-1-yl)methyl]-imidazole dihydrochloride (Compound 23) and clozapine were evaluated in the following models of learning and memory: a step-down passive avoidance task assay and a modified Morris water maze assay Separate groups of male Sprague Dawley rats were pretreated with either Compound 23 or clozapine prior to training in these tasks. The control compound, clozapine, produced an acquisition deficit in the passive avoidance task at the two highest doses tested (1.0, 2.0 mg/kg) but produced no significant deficits in retention. Clozapine produced no deficits in the water maze task at the doses tested. In the step-down passive avoidance assay animals that received the 0.25 mg/kg dose of Compound 23 showed significant improvement in memory compared to the vehicle group. Likewise in the modified Morris water maze, animals that received the 0.03, 0.25 and the 1.0 mg/kg dose of Compound 23 showed significant improvement in task retention compared to the vehicle group. These data show that Compound 23 does not impair learning, but enhances learning in animals.

METHOD

Non-naive male, Sprague Dawley rats (SASCO St. Louis) weighing between 2000–300 grams, were housed in groups of three in a temperature and humidity controlled vivarium having a 12 hour light/dark cycle. Animals had ad lib access to food and water.

Compound 23 was dissolved in 50% Polyethylene glycol (PEG) and administered in a dose range of 0.03–1.0 mg/kg. Clozapine was dissolved in 50% PEG and administered in a dose range of from 0.25 to 2mg/kg. Both drugs were administered intravenously 5 minutes prior to training in both learning tasks

APPARATUS

Step-Down Passive Avoidance:

A step-down passive avoidance platform 4 (cm)×7(cm) was placed in the center of an electrified gris floor, which was contained within a large (45×45×50 cm) white translucent plexiglas enclosure having a closable lid. The bars of the grip were spaced 1.5 cm apart and were wired to a BRS-LVE shock generator/scrambler which was set to deliver a 2mA 6 second shock. Four passive avoidance boxes were automated by customer software (Labview) and commercial interface modules (National Instruments) connected to a computer The timing and delivery of the shock as well as the latency to steo down and the number of trials taken to reach criterion during training was under the control of the computer. All testing was done in the presence of 62db white noise.

Modified Morris Water Maze:

A water maze apparatus consisted of a circular tank (120 cm in diameter and 56 cm in height) having a black interior. The tank was surrounded by external visual cues which consisted of a black and white checkered wall, a black and white striped wall, a while wall and a blue panel. The tank was filled with water (18°–20° C.) to a height of 52 cm and was divided into four quadrants (North, South, East and West). A black circular plexiglas platform (with black rubber top) was placed in the northeast quadrant approximately 1 cm below the surface of the water. The submerged platform was 51 cm in height and had a diameter of 9 cm. Training and testing was conducted in the presence of a 62db white noise source and under dim light conditions,

PROCEDURE:

1. Passive Avoidance:
Acquisition Training:

After pretreatment with clozapine, Compound 23 or control (vehicle), the animal was placed on the platform which automatically staged a timer. When the animal stepped off the platform it automatically received the footshock. Following each shock the animal was removed from the box and placed in its cage for a one minute intertrial interval and then returned to the platform. Training was terminated when the animal remained on the platform for 120 Seconds. Immediately after training the animal was returned to its home cage in a vivarium.

Retention Testing:

Testing was conduced approximately 24 hours after training, Drug-free animals were placed on the platform in the box in which they were trained and the latency to step down onto the unshocked floor was recorded for one trial. The animal was allowed to a maximum of 120 seconds to step down.

2. Modified Morris Water Maze:
Acquisition Training:

Acquisition training in this task assay consisted of either four or six training trials. The four trial procedure detects cognitive enhancing effects of drugs while the six trial procedure detects drugs that produce learning deficits in this task assay Compound 23 was tested in the water maze using a four trial procedure and clozapine using a six trial training procedure. Each animal was placed on the platform in the tank for 20 trials separated by an intertrial interval of 2 minutes. The staging position was pseudo-randomly varied but was the same order for each animal. During the ITI (intertrial interval) the animal was dried off and placed near a heat source (heat lamp). The latency to reach the submeged platform on each trial was measured and animals were allowed to remain on the platform for 10 seconds once they reach it. Since the platform was submerged just below the surface of the water, the animal was required to use the external visual cues surrounding the tank (distal cues) to locate the platform.

Retention Training:

On the following day, each animal was individually tested for retention in one trial. All animals were placed in the "SOUTH" starting position and latency to find the submerged platform was recorded.

RESULTS

Passive Avoidance:

There were no significant differences for acquisition between the vehicle group and animals treated with Compound 23. Animals that received 0.25 mg/kg dose of Compound 23 remained on the platform for a significantly longer time during retest than the vehicle animals. Animals that received the 1.0 mg/kg and 2.0 mg/kg doses of clozapine showed a significant deficit in acquisition compared to the vehicle group. There were no significant differences in retention between clozapine treated animals and the vehicle group.

Water Maze:

The difference between the first trial and the retest trial (latency to locate the platform on the following day) revealed significant improvement in retention relative to controls at the 0.03 mg/kd, 0.25 mg,/kg and the 1.0 mg/kg dose of Compound 23. However, the difference between the scores of trial 1 and the retest trial for animals that received clozapine revealed no significant differences.

These results indicate that compound 23 improved memory in mammals. These results further show that compound 23 also enhances learning in mammals. Thus, the compounds of the invention are useful for enhancing cognition in mammals and can be used in methods for enhancing cognition, specifically teaming and memory, in mammals.

The disclosures in this application of all articles and references, including patents, are incorporated herein by reference.

The invention, and the manner and process of making and using it, are now described in such full, clear, concise and exact terms as to enable any person skilled in the art to which it pertains, to make and use the same. It is to be understood that the foregoing describes preferred embodiments of the present invention and that modifications may be made therein without departing from the spirit or scope of the present invention as set forth in the claims. To particularly point out and distinctly claim the subject matter regarded as invention, the following claims conclude this specification.

What is claimed is:

1. A compound of the formula:

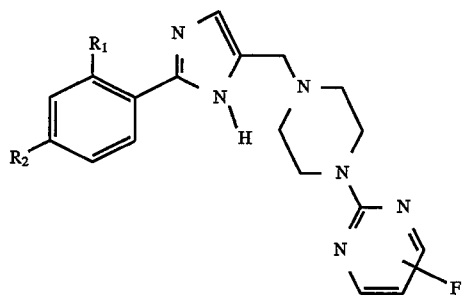

or the pharmaceutically acceptable salts thereof wherein $R_1$ and $R_2$ are independently selected from hydrogen and fluoro with the proviso that at least one of the $R_1$ and $R_2$ is fluoro.

2. A compound according to claim 1 which is 2-(4-Fluorophenyl-4(5) -[(4-(5-fluoro-2-pyrimidinyl)-piperazin -1-yl)-methyl]-imidazole.

3. A compound according to claim 1 which is [2-(4-Fluorophenyl-4(5)-[(4-(4-fluoro-2-pyrimidinyl)-piperazin-1-yl)-methyl]-imidazole] 2-(4-Fluorophenyl-4(5)-[(4-(5-fluoro-2-pyrimidinyl)-piperazin-1-yl)-methyl]-imidazole.

* * * * *